(12) United States Patent
Iwase et al.

(10) Patent No.: US 12,276,630 B2
(45) Date of Patent: Apr. 15, 2025

(54) OIL FILM STATE DETECTION METHOD, STATE DETECTION DEVICE, AND PROGRAM

(71) Applicant: NSK LTD., Tokyo (JP)

(72) Inventors: Shunsuke Iwase, Kanagawa (JP); Taisuke Maruyama, Kanagawa (JP)

(73) Assignee: NSK LTD., Tokyo (JP)

( * ) Notice: Subject to any disclaimer, the term of this patent is extended or adjusted under 35 U.S.C. 154(b) by 125 days.

(21) Appl. No.: 18/246,990

(22) PCT Filed: Sep. 24, 2021

(86) PCT No.: PCT/JP2021/035206
§ 371 (c)(1),
(2) Date: Mar. 28, 2023

(87) PCT Pub. No.: WO2022/071164
PCT Pub. Date: Apr. 7, 2022

(65) Prior Publication Data
US 2023/0408435 A1    Dec. 21, 2023

(30) Foreign Application Priority Data
Sep. 29, 2020 (JP) .................... 2020-163963
Aug. 25, 2021 (JP) .................... 2021-137564

(51) Int. Cl.
*G01N 27/22* (2006.01)
*F16C 33/66* (2006.01)

(52) U.S. Cl.
CPC ........ *G01N 27/221* (2013.01); *F16C 33/6688* (2013.01)

(58) Field of Classification Search
None
See application file for complete search history.

(56) References Cited

U.S. PATENT DOCUMENTS 5,001,435 A * 3/1991 Smith .................... G01B 7/144
324/683
7,043,402 B2 * 5/2006 Phillips .................. G01N 27/02
702/65

(Continued)

FOREIGN PATENT DOCUMENTS

JP    2005-308714 A    11/2005
JP    2007-310611 A    11/2007

(Continued)

OTHER PUBLICATIONS

Translation of WO 2018/128062 A1 (Year: 2018).*

(Continued)

*Primary Examiner* — Jermele M Hollington
(74) *Attorney, Agent, or Firm* — Sughrue Mion, PLLC

(57) ABSTRACT

There is provided a state detection method for detecting an oil film state according to a lubricant in a device configured to lubricate a plurality of parts with the lubricant, the method including: a measurement step of measuring impedance and a phase angle of an electric circuit by applying an AC voltage to the electric circuit configured with the plurality of parts while changing a frequency; and a derivation step of deriving an oil film thickness according to the lubricant and a parameter indicating an electrical characteristic according to the oil film thickness, based on a relative dielectric constant at a high frequency limit of the lubricant defined based on a composition of the lubricant, and the impedance and the phase angle measured in the measurement step.

6 Claims, 13 Drawing Sheets

(56) References Cited

U.S. PATENT DOCUMENTS

| | | | |
|---|---|---|---|
| 10,429,373 B2 | 10/2019 | Maeda et al. | |
| 2009/0315574 A1 | 12/2009 | Akiyama et al. | |
| 2019/0128866 A1* | 5/2019 | Maeda | G01M 13/04 |
| 2022/0074813 A1 | 3/2022 | Maruyama et al. | |
| 2023/0366750 A1* | 11/2023 | Iwase | F16C 33/6633 |
| 2023/0366781 A1* | 11/2023 | Maruyama | G01M 13/04 |
| 2024/0255030 A1* | 8/2024 | Maruyama | F16C 19/52 |

FOREIGN PATENT DOCUMENTS

| | | | | |
|---|---|---|---|---|
| JP | 2009-2693 A | 1/2009 | | |
| JP | 2019-82448 A | 5/2019 | | |
| JP | 2019-211317 A | 12/2019 | | |
| WO | WO-2018128062 A1 * | 7/2018 | | G01M 13/04 |
| WO | 2020/149233 A1 | 7/2020 | | |

OTHER PUBLICATIONS

Maruyama et al., "In Situ Quantification of Oil Film Formation and Breakdown in EHD Contacts," Tribology Transactions, vol. 61, No. 6, pp. 1057-1066, Jul. 3, 2018, Total 11 pages, Retrieved from the Internet: <https://www.tandfonline.com/doi/pdf/10.1080/10402004. 2018.1468519?needAccess=true>.

International Search Report (PCT/ISA/210) dated Nov. 30, 2021, issued by the International Searching Authority in counterpart International Application No. PCT/JP2021/035206.

Written Opinion (PCT/ISA/237) dated Nov. 30, 2021, issued by the International Searching Authority in counterpart International Application No. PCT/JP2021/035206.

European Extended Search Report issued Feb. 27, 2024 by the European Patent Office for EP Patent Application No. 21875466.1.

* cited by examiner

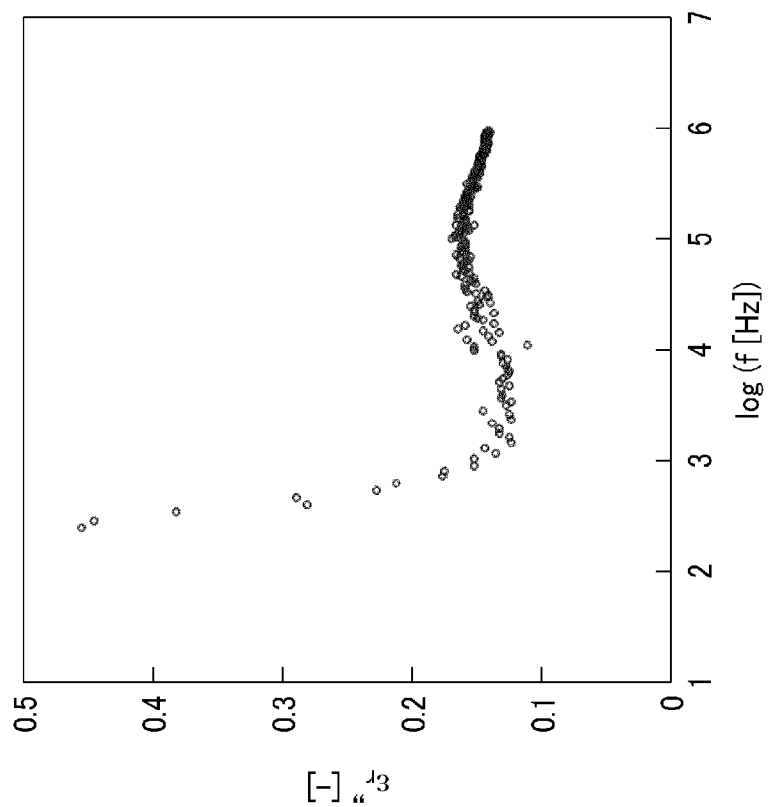
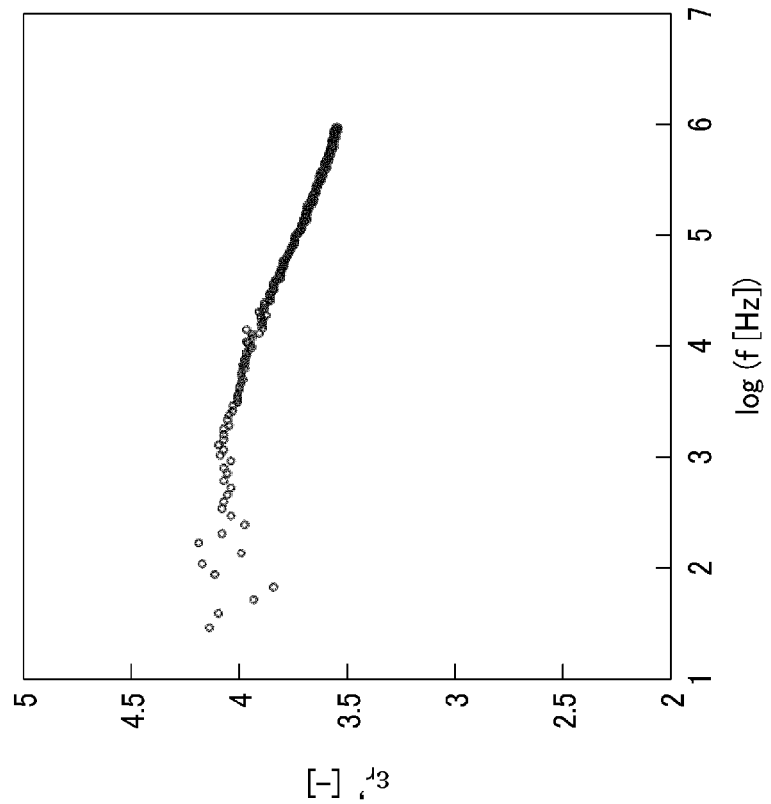
FIG. 6A
FIG. 6B

FIG. 9

| | | |
|---|---|---|
| RELATIVE DIELECTRIC CONSTANT (LOW FREQUENCY LIMIT) | $\varepsilon_{r0}$ [−] | 4.29 |
| RELATIVE DIELECTRIC CONSTANT (HIGH FREQUENCY LIMIT) | $\varepsilon_{r\infty}$ [−] | 3.27 |
| RELAXATION STRENGTH | $\varepsilon_{r0} - \varepsilon_{r\infty}$ | 1.02 |
| RELAXATION TIME | $\tau$ [μs] | 1.20 |
| CONSTANT REPRESENTING DISTRIBUTION OF RELAXATION TIME | $\beta$ [−] | 0.39 |
| DC CONDUCTIVITY | $\sigma_0$ [nS/m] | 6.80 |

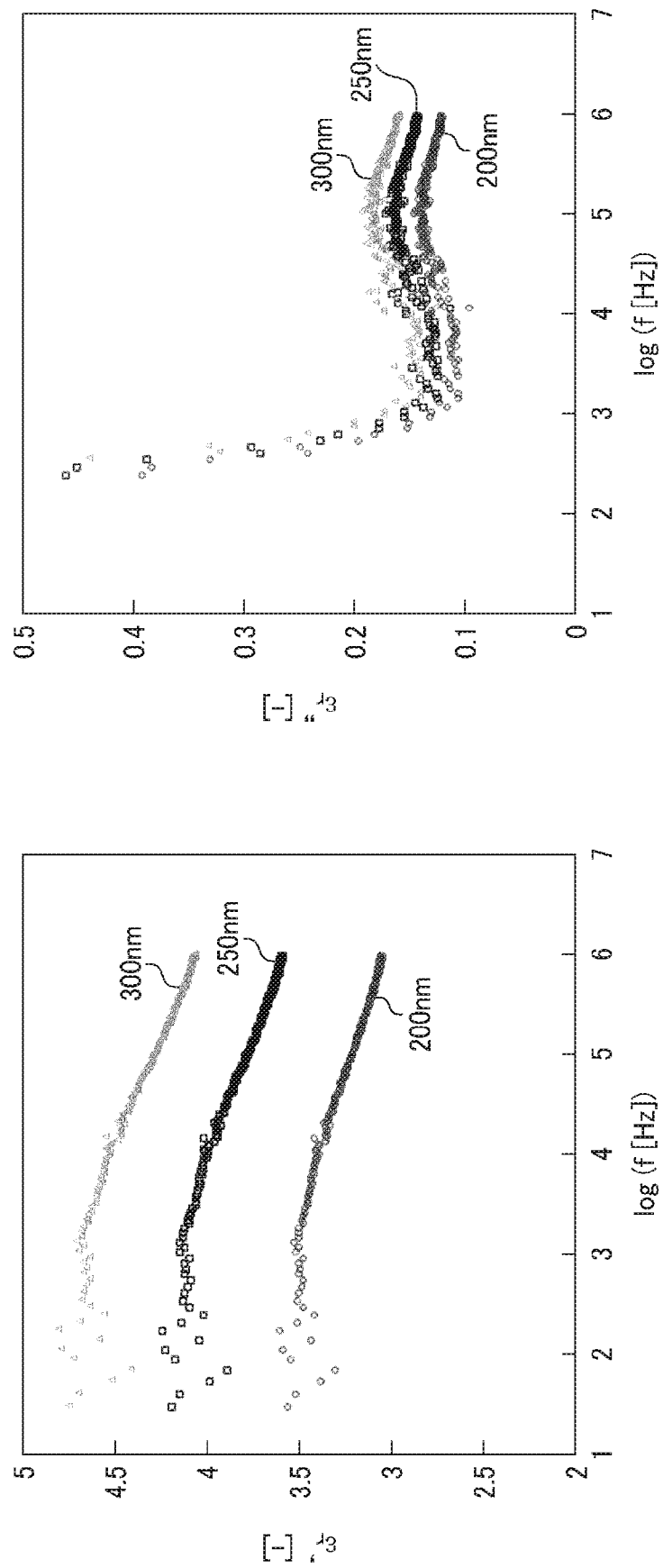

FIG. 12

| RELATIVE DIELECTRIC CONSTANT (LOW FREQUENCY LIMIT) | $\varepsilon_{r0}$ [-] | 4.20 |
|---|---|---|
| RELATIVE DIELECTRIC CONSTANT (HIGH FREQUENCY LIMIT) | $\varepsilon_{r\infty}$ [-] | 3.23 (FIXED IN BULK STATE) |
| RELAXATION STRENGTH | $\varepsilon_{r0}-\varepsilon_{r\infty}$ | 0.97 |
| RELAXATION TIME | $\tau$ [μs] | 1.20 |
| CONSTANT REPRESENTING DISTRIBUTION OF RELAXATION TIME | $\beta$ [-] | 0.39 |
| DC CONDUCTIVITY | $\sigma_0$ [nS/m] | 6.80 |
| OIL FILM THICKNESS | $h$ [nm] | 245.1 |

OIL FILM STATE DETECTION METHOD, STATE DETECTION DEVICE, AND PROGRAM

CROSS-REFERENCE TO RELATED APPLICATIONS

This application is a National Phase Entry of PCT International Application No. PCT/JP2021/035206, filed on Sep. 24, 2021, which claims priority to Japanese Patent Application No. 2020-163963, filed on Sep. 29, 2020, and Japanese Patent Application No. 2021-137564, filed on Aug. 25, 2021, the contents of all of which are incorporated herein by reference in their entirety.

TECHNICAL FIELD

The present invention relates to an oil film state detection method, a state detection device, and a program.

BACKGROUND ART

In the related art, in bearing devices, a configuration in which a lubricant (for example, lubricating oil or grease) is used to lubricate rotation has been widely used. On the other hand, by periodically diagnosing a state of rotating parts such as bearing devices, damage and wear can be detected at an early stage to suppress failures of the rotating parts from occurring.

The bearing device using a lubricant is required to appropriately detect the internal state for diagnosing the operating state. For example, Patent Literature 1 discloses a method for detecting an oil film thickness of a lubricant and a metal contact ratio in a rolling device.

CITATION LIST

Patent Literature

Patent Literature 1: JP2019-211317A

SUMMARY OF INVENTION

Technical Problem

It is very useful to grasp conditions around a lubricant in a device such as a bearing device to suppress damage to the device. In a method of Patent Literature 1, although a film thickness of a lubricant and a metal contact ratio can be derived, parameters related to electrical characteristics of the rolling bearing are not derived. In the first place, since it is difficult to actually measure an oil film thickness of a lubricant in a rolling bearing during rotation, it is also difficult to derive electrical characteristics according to the oil film thickness.

In view of the above-described problems, the present invention is to provide a method for deriving a film thickness of a lubricant and a parameter related to an electrical characteristic according to the film thickness in a device such as a rolling bearing.

Solution to Problem

To solve the above-described problems, the present invention has the following configuration. That is, there is provided a state detection method for detecting an oil film state according to a lubricant in a device configured to lubricate a plurality of parts with the lubricant, the method including:
a measurement step of measuring impedance and a phase angle of an electric circuit by applying an AC voltage to the electric circuit configured with the plurality of parts while changing a frequency; and
a derivation step of deriving an oil film thickness according to the lubricant and a parameter indicating an electrical characteristic according to the oil film thickness, based on a relative dielectric constant at a high frequency limit of the lubricant defined based on a composition of the lubricant, and the impedance and the phase angle measured in the measurement step.

Another aspect of the present invention has the following structures. That is, there is provided a state detection device configured to detect an oil film state according to a lubricant in a device configured to lubricate a plurality of parts with the lubricant, the device including:
a measurement unit configured to measure impedance and a phase angle of an electric circuit by applying an AC voltage to the electric circuit configured with the plurality of parts while changing a frequency; and
a derivation unit configured to derive an oil film thickness according to the lubricant and a parameter indicating an electrical characteristic according to the oil film thickness, based on a relative dielectric constant at a high frequency limit of the lubricant defined based on a composition of the lubricant, and the impedance and the phase angle measured in by the measurement unit.

Another aspect of the present invention has the following structures. That is, there is provided a non-transitory computer-readable storage medium storing a computer program for causing a computer to execute:
a measurement step of measuring impedance and a phase angle of an electric circuit by applying an AC voltage to the electric circuit configured with a plurality of parts while changing a frequency for a device configured to lubricate the plurality of parts with a lubricant; and
a derivation step of deriving an oil film thickness according to the lubricant and a parameter indicating an electrical characteristic according to the oil film thickness, based on a relative dielectric constant at a high frequency limit of the lubricant defined based on a composition of the lubricant, and the impedance and the phase angle measured in the measurement step.

Advantageous Effects of Invention

According to the present invention, it is possible to provide a method for deriving a film thickness of a lubricant in a device and a parameter related to an electrical characteristic according to the film thickness.

BRIEF DESCRIPTION OF DRAWINGS

FIGS. 6A and 6B are diagrams illustrating a relationship between frequency, a relative dielectric constant, and a relative dielectric loss factor.

FIG. 9 is a diagram illustrating an example of parameter derivation by fitting to a theoretical formula.

FIGS. 10A and 10B are diagrams illustrating a relative dielectric constant and a relative dielectric loss factor for each oil film thickness.

FIG. 12 is a diagram illustrating an example of oil film thickness and parameter derivation.

DESCRIPTION OF EMBODIMENTS

Hereinafter, an aspect for implementing the present invention is described with reference to drawings. Note that the embodiment described below is one embodiment for describing the invention of the present application, and is not intended to be construed as limiting the invention of the present application, and all configurations described in the embodiments are not essential configurations for solving the problems of the present invention. In each drawing, the same component is denoted by the same reference number to indicate correspondence.

First Embodiment

Hereinafter, a first embodiment according to the present invention will be described. Note that, in the following description, a ball bearing is used as an example of a rolling bearing, but the present invention is not limited thereto, and can be applied to rolling bearings having other configurations. For example, as types of the rolling bearings to which the present invention can be applied, there are exemplified deep groove ball bearings, angular contact ball bearings, tapered roller bearings, cylindrical roller bearings, and self-aligning roller bearings.

[Device Configuration]

Figure 1:
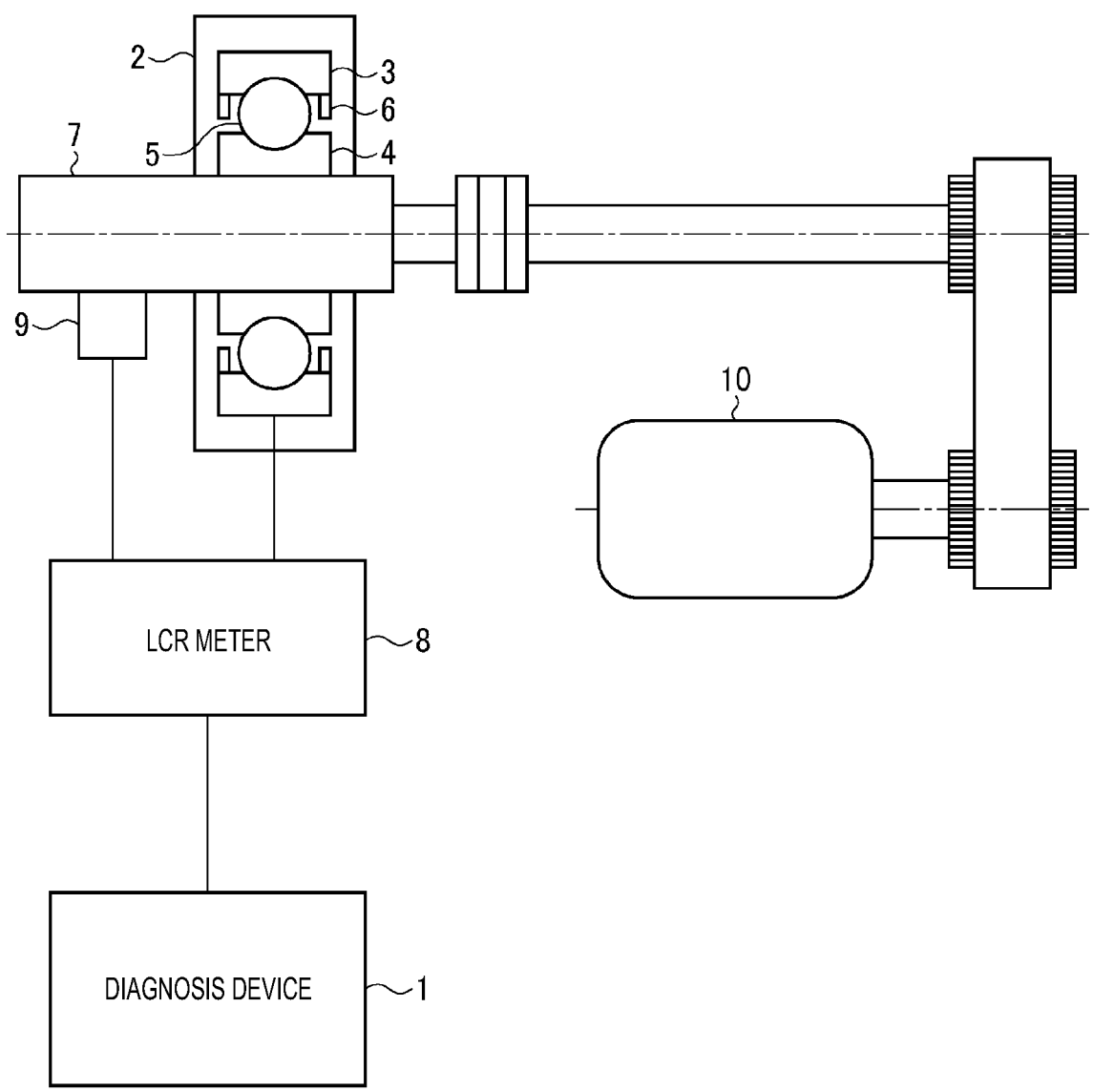
FIG. 1 is a schematic diagram illustrating an example of a configuration of an apparatus for diagnosis according to the present invention.

FIG. 1 is a schematic configuration diagram illustrating an example of the overall configuration when performing diagnosis with a diagnosis device 1 according to the present embodiment. In FIG. 1, a bearing device 2 to which a state detection method according to the present embodiment is applied and the diagnosis device 1 performing state detection and diagnosis, are illustrated. Note that the configuration illustrated in FIG. 1 is an exemplary one, and a different configuration may be used according to a configuration of the bearing device 2 and the like. Although FIG. 1 illustrates a configuration in which the bearing device 2 includes one rolling bearing, the present invention is not limited thereto, and one bearing device 2 may include a plurality of rolling bearings.

In the bearing device 2, the rolling bearings rotatably support a rotating shaft 7. The rotating shaft 7 is supported by a housing (not illustrated) that covers an outside of the rotating shaft 7 via the rolling bearing that is a rotating component. The rolling bearing includes an outer ring (outer member) 3 which is a fixing ring fitted inside the housing, an inner ring (inner member) 4 which is a rotating ring fitted on the rotating shaft 7, a plurality of balls (rollers) which are a plurality of rolling elements 5 arranged between the inner ring 4 and the outer ring 3, and a holder (not illustrated) holding the rolling elements 5 so that rolling elements can roll. Herein, although the outer ring 3 is fixed in the above-described configuration, the inner ring 4 may be fixed, and the outer ring 3 may be rotated in the other configurations. A seal 6 is provided as a peripheral member for suppressing dust from entering the vicinity of the rolling elements 5 and lubricant from leaking. Friction between the inner ring 4 and the rolling elements 5 and friction between the outer ring 3 and the rolling elements 5 are reduced by a predetermined lubrication method inside the rolling bearing. Although the lubrication method is not particularly limited, for example, grease lubrication, oil lubrication, or the like is used and is supplied to the inside of the rolling bearing. The type of lubricant is not particularly limited.

A motor 10 is a driving motor, and supplies power to the rotating shaft 7 by rotation. The rotating shaft 7 is connected to an LCR meter 8 via a rotation connector 9. The rotation connector 9 may be configured by using, for example, carbon brushes, but is not limited thereto. The bearing device 2 is also electrically connected to the LCR meter 8, and the LCR meter 8 also functions as an AC power source for the bearing device 2 here.

The diagnosis device 1 operates as a detection device capable of executing a detection method according to the present embodiment. When diagnosing, the diagnosis device 1 instructs the LCR meter 8 with an angular frequency ω of the AC power source and an AC voltage V as inputs and acquires impedance |Z| (|Z| denotes an absolute value of Z) of the bearing device 2 and a phase angle θ as outputs to the instruction from the LCR meter 8. Then, the diagnosis device 1 detects information about the state of the lubricant in the bearing device 2 by using the above values. Details of the detection method will be described later.

The diagnosis device 1 may be realized by, for example, an information processing device including a control device, a storage device, and an output device (not illustrated). The control device may be configured with a central processing unit (CPU), a micro processing unit (MPU), a digital single processor (DSP), a dedicated circuit, or the like. The storage device is configured with volatile and non-volatile storage media such as a hard disk drive (HDD), a read only memory (ROM), a random access memory (RAM), or the like, and various information can be input and output according to instructions from the control device. The output device is configured with a speaker, a light, a display device such as a liquid crystal display, or the like and notifies an operator according to the instruction from the control device. A notification method by the output device is not particularly limited, but for example, auditory notification by sound may be used, or visual notification by screen output may be used. The output device may be a network interface having a communication function and may perform a notification operation by transmitting data to an external device (not illustrated) via a network (not illustrated). A content of notification herein is not limited to notification indicating abnormality detected if the abnormality is diagnosed based on a detection result, but may include notification indicating that the bearing device 2 is normal.

[Physical Model]

Figure 2:
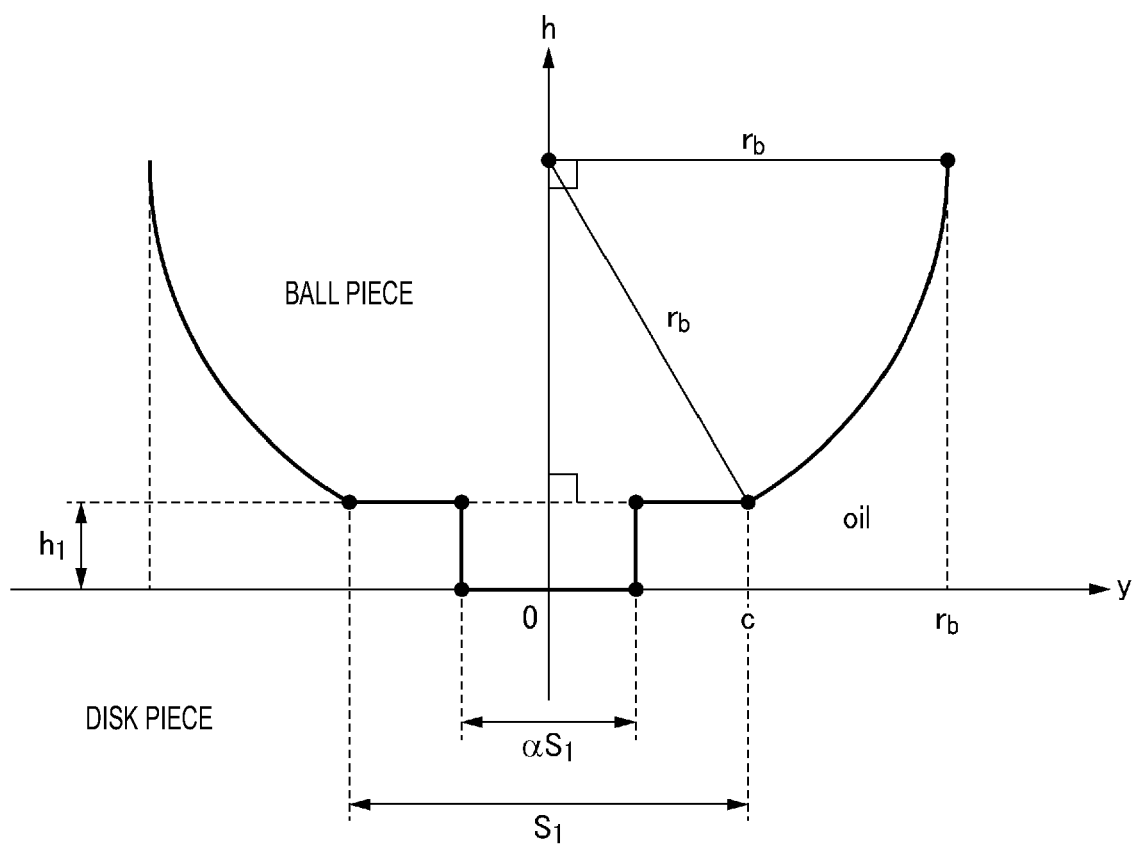
FIG. 2 is a graph illustrating a physical model of a bearing device according to the present invention.

The state of contact between the rolling elements 5 and the outer ring 3 (or the inner ring 4) in the bearing device 2 will be described with reference to FIG. 2. FIG. 2 is a graph illustrating a physical model when a ball piece and a disk piece come into contact with each other. The ball piece corresponds to the rolling element, and the disk piece corresponds to the outer ring 3 (or inner ring 4). An h-axis indicates an oil film thickness direction, and a y-axis indicates a direction perpendicular to the oil film thickness direction. Variables illustrated in FIG. 2 are as follows.

$S_1$: Hertzian contact area (Hertzian contact region)
c: Hertzian contact circle radius ($=\sqrt{S_1/\pi}$)
α: break rate of oil film (metal contact ratio) (0≤α<1)
$r_b$: radius of ball piece
$\alpha S_1$: actual contact area (break region of oil film)
h: oil film thickness
$h_1$: oil film thickness in Hertzian contact region In the Hertzian contact region, a ratio of an area with metal contact and an area without metal contact is α:(1−α). In an ideal state where the ball piece and the disk piece are not in contact with each other, α=0 is satisfied, and when y=0, h>0 is satisfied.

The oil film thickness h illustrated in FIG. 2 is represented by the following formula.

$$h=0 (-\alpha S_1/2 \leq y \leq \alpha S_1/2)$$

$$h=h_1 (-c \leq y < -\alpha S_1/2 \text{ or } \alpha S_1/2 < y \leq c)$$

$$h=h_1+\sqrt{(r_b^2-c^2)}-\sqrt{(r_b^2-y^2)} (-r_b \leq y < -c \text{ or } c < y \leq r_b) \quad (1)$$

Note that, in an actual rolling bearing, since the rolling elements 5 are elastically deformed when receiving a load, strictly speaking, the rolling elements 5 are not spherical bodies; but in the present embodiment, the above-mentioned formula (1) can be used for spherical bodies. Therefore, the formula used when obtaining the oil film thickness is not limited to formula (1), and other calculation formulas may be used.

Figure 3:
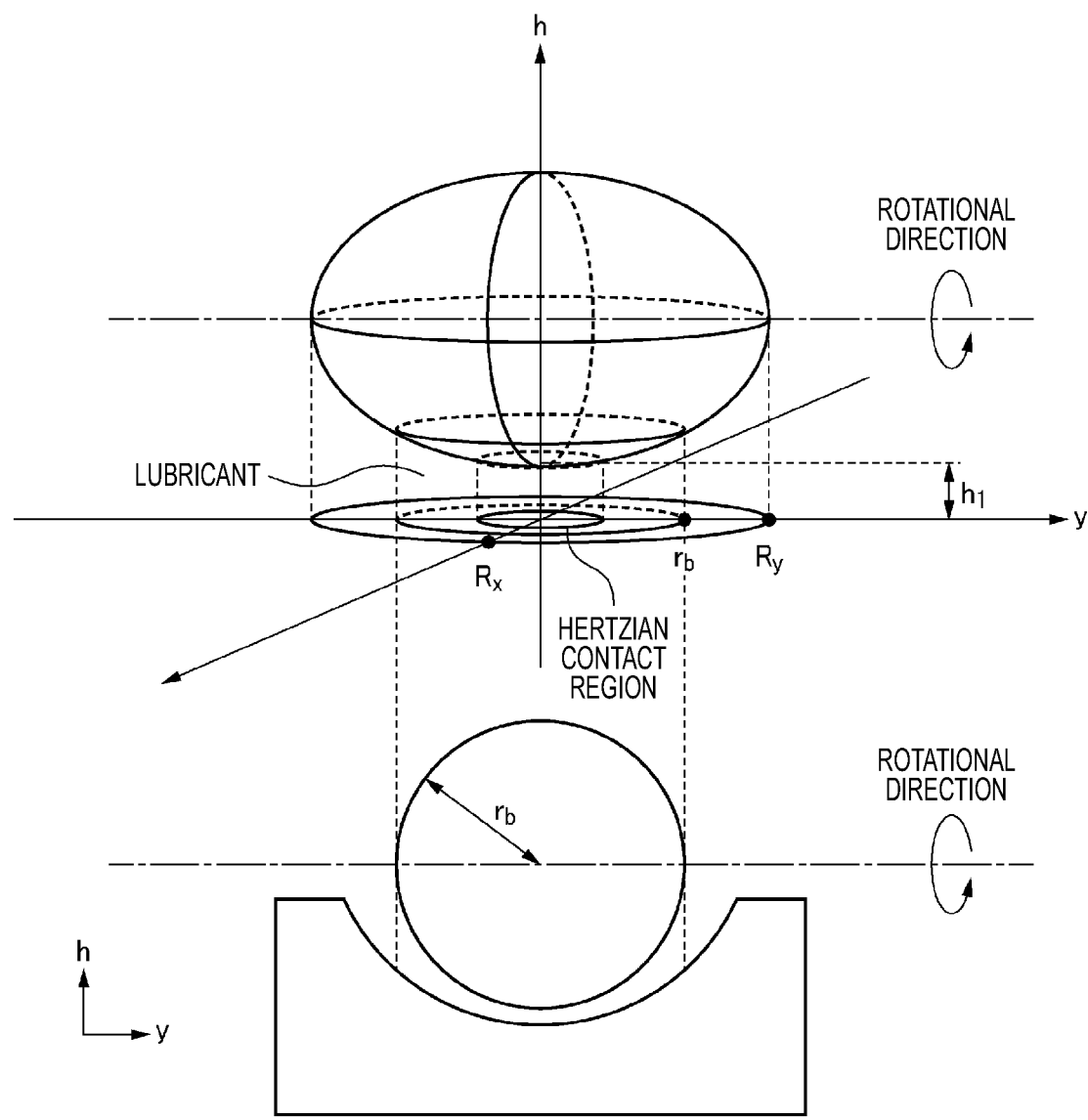
FIG. 3 is a graph illustrating a geometric model according to the present invention.

FIG. 3 is a diagram illustrating a geometric model of the rolling bearing. The x-axis indicates an axial direction perpendicular to each of the y-axis and the h-axis. Variables illustrated in FIG. 3 are as follows. The same symbols as those in FIG. 2 correspond to each other.

$R_x$: effective radius (x-axis)
$R_y$: effective radius (y-axis)
$h_1$: oil film thickness in Hertzian contact region
$r_b$: radius of ball piece As illustrated in FIG. 3, description is made while the rolling elements 5 is assumed to rotate around a y-axis and a load (axial load) is assumed to be applied in the y-axis direction.

[Equivalent Electric Circuit]

Figure 4:
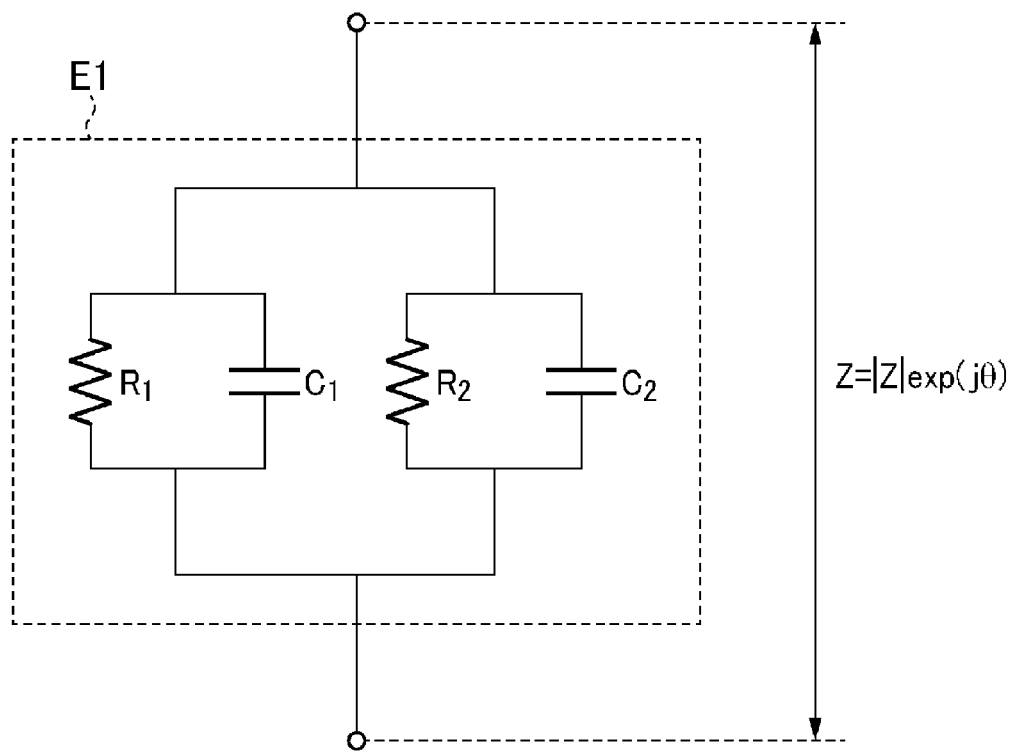
FIG. 4 is a circuit diagram illustrating an equivalent circuit of the bearing device according to the present invention.

FIG. 4 is a diagram illustrating an electrically equivalent electric circuit (equivalent circuit) of the physical model illustrated in FIG. 2. An equivalent circuit E1 is configured with a resistor $R_1$ a resistor $R_2$, a capacitor $C_1$, and a capacitor $C_2$. The resistor $R_1$ corresponds to a resistance in a break region ($=\alpha S_1$). The resistor $R_2$ corresponds to a resistance around the break region. The capacitor $C_1$ corresponds to a capacitor formed by the oil film in the Hertzian contact region and is denoted by a capacitance $C_1$. The capacitor $C_2$ corresponds to a capacitor formed by the oil film around the Hertzian contact region ($-r_b \leq y < -c$ and $c < y \leq r_b$ in FIG. 2) and is denoted by a capacitance $C_2$. The Hertzian contact region ($=S_1$) forms a parallel circuit of the resistor $R_1$ and the capacitor $C_1$ in the equivalent circuit E1 of FIG. 4. A periphery of the Hertzian contact region forms a parallel circuit of the resistor $R_2$ and the capacitor $C_2$ in the equivalent circuit E1 of FIG. 4. The equivalent circuit E1 is formed by connecting the parallel circuits in parallel. Here, it is assumed that the periphery of the Hertzian contact region ($-r_b \leq y < -c$ and $c < y \leq r_b$ in FIG. 2) is filled with the lubricant.

The impedance of the equivalent circuit E1 is denoted by Z. Herein, an AC voltage V applied to the equivalent circuit E1, a current I flowing through the equivalent circuit E1, and a complex impedance Z of the entire equivalent circuit E1 are expressed by the following formulas (2) to (4).

$$V=|V|\exp(j\omega t) \quad (2)$$

$$I=|I|\exp(j\omega t-j\theta) \quad (3)$$

$$Z=V/I=|V/I|\exp(j\theta)=|Z|\exp(j\theta) \quad (4)$$

j: imaginary number
ω: angular frequency of AC voltage
t: time
θ: phase angle (phase shift between voltage and current)

Figure 5:
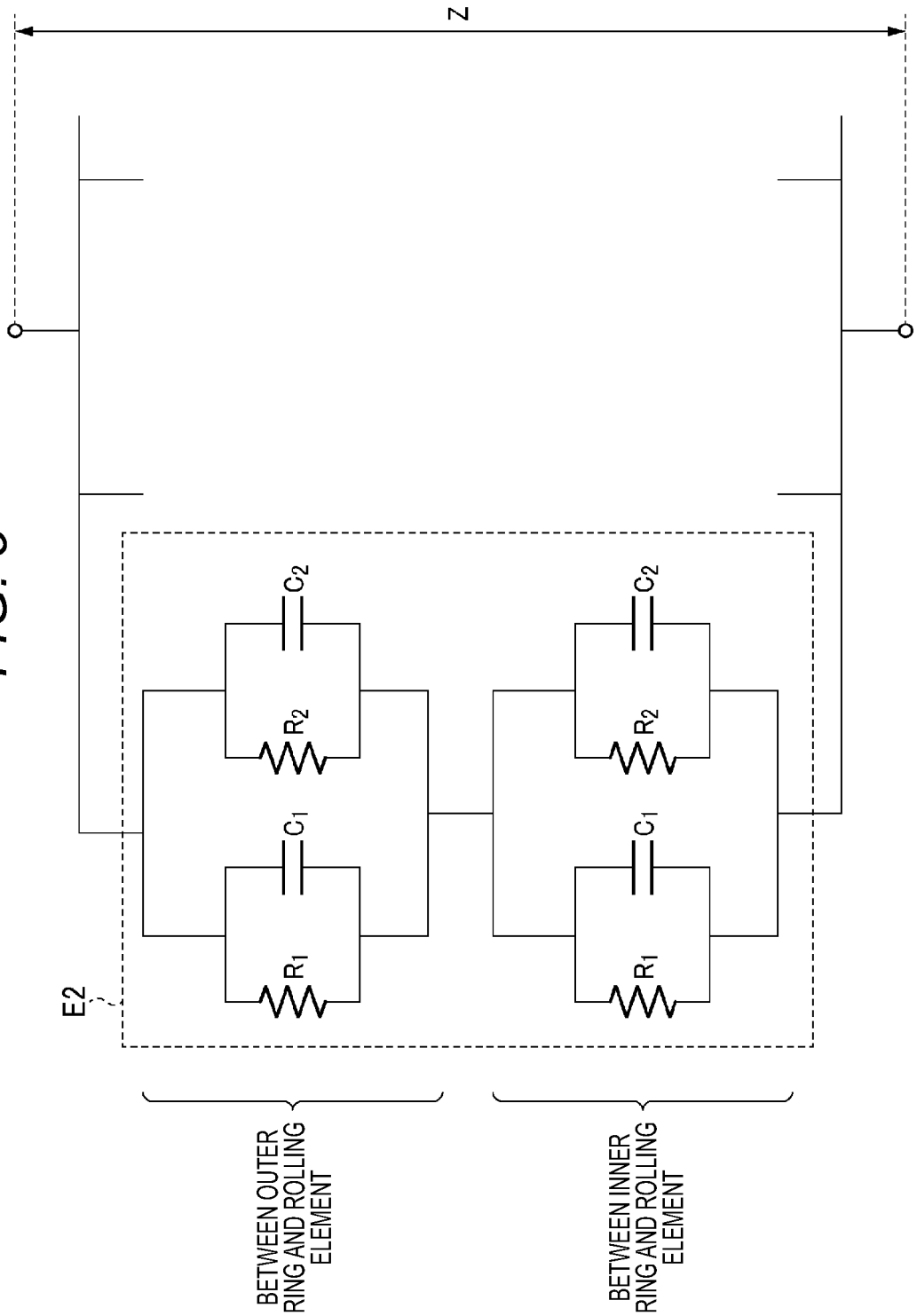
FIG. 5 is a circuit diagram illustrating an equivalent circuit of the bearing device according to the present invention.

FIG. 5 is a diagram illustrating an electrically equivalent electric circuit around one rolling element 5 based on the equivalent circuit E1 illustrated in FIG. 4. Focusing on the one rolling element 5, an equivalent circuit E2 is formed between the outer ring 3 and the rolling elements 5 and between the inner ring 4 and the rolling elements 5. Herein, although description is made while the electric circuit formed by the outer ring 3 and the rolling elements 5 is assumed to be formed on the upper side and the electric circuit formed by the inner ring 4 and the rolling elements 5 is assumed to be formed on the lower side, the reversed arrangement may be used. Around the one rolling element 5, the electric circuits are connected in series to form the equivalent circuit E2.

[Oil Film Dielectric Constant Under Axial Load]

In the present embodiment, the relative dielectric constant and the relative dielectric loss factor in a state where the axial load is applied to the rolling bearing via the rotating shaft 7 will be described. According to the equivalent circuit E2 illustrated in FIG. 5, the values of the resistors and the capacitors are defined by the following formulas.

[Formula 1]

$$\frac{1}{R_1}+\frac{1}{R_2}=\frac{I\cos\theta}{kn|Z|} \quad (5)$$

[Formula 2]

$$C_1+C_2=-\frac{I\sin\theta}{kn\omega|Z|} \quad (6)$$

[Formula 3]

$$C_1=\varepsilon'\frac{S}{h} \quad (7)$$

[Formula 4]

$$C_2=2\pi\varepsilon'\frac{r_x r_y}{r}\left\{\ln\left(\frac{r}{h}\right)-1\right\} \quad (8)$$

[Formula 5]

$$\frac{1}{R_1}=\omega\varepsilon''\frac{S}{h} \quad (9)$$

[Formula 6]

$$\frac{1}{R_2}=2\pi\omega\varepsilon''\frac{r_x r_y}{r}\left\{\ln\left(\frac{r}{h}\right)-1\right\} \quad (10)$$

ε: dielectric constant of oil film (lubricant)
ε': relative dielectric constant of oil film ε': relative dielectric loss factor of oil film
Z: impedance of entire circuit
$R_1$: resistance at Hertzian contact region
$R_2$: resistance around Hertzian contact region
$C_1$: capacitance at Hertzian contact region
$C_2$: capacitance around Hertzian contact region
S: Hertzian contact area
k: number of rolling bearings
n: total number of rolling elements
l: number of contact areas per rolling element
ω: angular frequency of AC voltage
θ: phase angle
h: oil film thickness
r: effective radius of rolling element
$r_x$: effective radius of rolling element (x-axis)
$r_y$: Effective radius of rolling element (y-axis)
π: circumference ratio
ln: logarithmic function The following formulas are obtained by rearranging a relative dielectric constant ε' and a relative dielectric loss factor ε" based on the above-described formulas (5) to (10).

[Formula 7]

$$\varepsilon' = -\frac{l}{kn} \cdot \frac{\sin\theta}{\omega|Z|} \cdot \frac{1}{\frac{S}{h} + 2\pi\left(\frac{r_x r_y}{r}\right)\left\{\ln\left(\frac{r}{h}\right) - 1\right\}} \quad (11)$$

[Formula 8]

$$\varepsilon'' = -\frac{l}{kn} \cdot \frac{\cos\theta}{\omega|Z|} \cdot \frac{1}{\frac{S}{h} + 2\pi\left(\frac{r_x r_y}{r}\right)\left\{\ln\left(\frac{r}{h}\right) - 1\right\}} \quad (12)$$

In the present embodiment, the above-described formulas (11) and (12) are used in deriving the relative dielectric constant and the relative dielectric loss factor of the rolling bearing under the axial load.

[Relative Dielectric Constant and Relative Dielectric Loss Factor]

FIGS. 6A and 6B are diagrams illustrating a tendency of changes in relative dielectric constant and relative dielectric loss factor according to a change in frequency. Herein, in the configuration illustrated in FIG. 1, the relative dielectric constant $\varepsilon_r'$ and the relative dielectric loss factor $\varepsilon_r''$ of the lubricant in the rolling bearing are measured by performing tests under the following conditions, and a dielectric relaxation phenomenon due to the lubricant in the rolling bearing is confirmed. Here, the relative dielectric constant $\varepsilon_r'$ and the relative dielectric loss factor $\varepsilon_r''$ are derived by using the above-described formulas (11) and (12). Herein, as an example, the oil film thickness h in the formulas (7) and (8) is set to 250 nm.

(Test Condition)
  bearing: deep groove ball bearing (brand number: 6306)
  rotation speed: 997 [$min^{-1}$]
  axial load: 1000 [N]
  radial load: 0 [N]
  temperature: 23 [° C.]
  lubricant: 12-OH stearic acid grease
  lubricant base oil: ester oil
  AC voltage: 1.0 [V]
  AC power frequency: 20 to 1 M [Hz]

In FIG. 6A, the horizontal axis indicates a logarithm of a frequency [Hz], and the vertical axis indicates the relative dielectric constant $\varepsilon_r'$. FIG. 6A illustrates experimental values obtained as the above-described test results. As illustrated in FIG. 6A, the relative dielectric constant $\varepsilon_r'$ tends to decrease (monotonically decrease) as the frequency increases.

In FIG. 6B, the horizontal axis indicates the logarithm of the frequency [Hz], and the vertical axis indicates the relative dielectric loss factor $\varepsilon_r''$. FIG. 6B illustrates experimental values obtained as the above-described test results. As illustrated in FIG. 6B, after the relative dielectric loss factor $\varepsilon_r''$ once decreases as the frequency increases, the relative dielectric loss factor tends to rise and, after that, decrease again.

[Application to Theoretical Formula]

Next, derivation of parameters related to the dielectric relaxation phenomenon due to the lubricant in the rolling bearing will be described. Due to the dielectric relaxation phenomenon of the lubricant in the rolling bearing, the relative dielectric constant and the relative dielectric loss factor tend to change as illustrated in FIGS. 6A and 6B. To specify such change tendency, various parameters are derived by applying (fitting) to the theoretical formula. In the present embodiment, a relative dielectric constant $\varepsilon_{r0}$ at a low frequency limit, a relative dielectric constant $\varepsilon_{r\infty}$ at a high frequency limit, a relaxation strength ($\varepsilon_{r0} - \varepsilon_{r\infty}$), a relaxation time τ, and a constant β representing a distribution of the relaxation time, and DC conductivity co as parameters that are derivation targets are described. In the present embodiment, the following theoretical formula is used.

[Formula 9]

$$\varepsilon_r' = \frac{1}{2}(\varepsilon_{r0} - \varepsilon_{r\infty})\left\{1 - \frac{\sinh\beta X}{\cosh\beta X + \cos\left(\frac{\beta\pi}{2}\right)}\right\} + \varepsilon_{r\infty} \quad (13)$$

[Formula 10]

$$\varepsilon_r'' = \frac{\sigma_0}{2\pi f \varepsilon_0} + \frac{1}{2}(\varepsilon_{r0} - \varepsilon_{r\infty})\frac{\sinh\left(\frac{\beta\pi}{2}\right)}{\cosh\beta X + \cos\left(\frac{\beta\pi}{2}\right)} \quad (14)$$

[Formula 11]

$$X = \ln(\omega\tau) = \ln(2\pi f \tau) \quad (15)$$

Figure 7A:
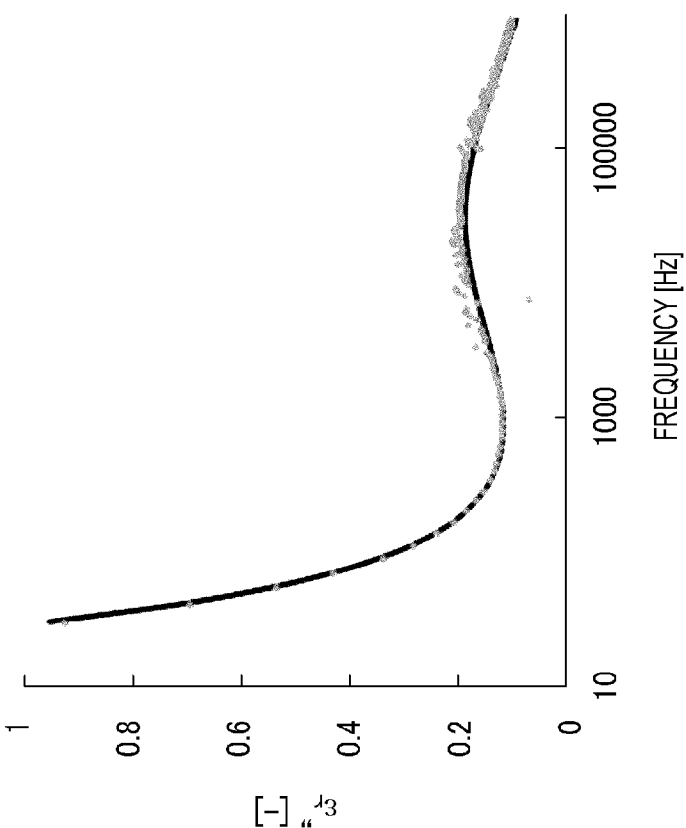
FIGS. 7A and 7B are diagrams each illustrating derivation of parameters by fitting to a theoretical formula.
Figure 7B:
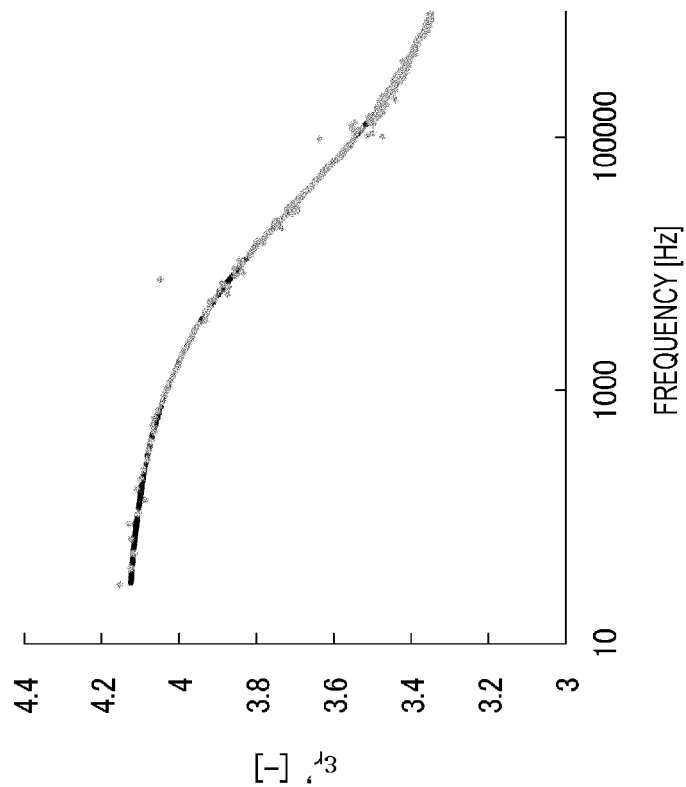

$\varepsilon_{r0}$: relative dielectric constant at low frequency limit
$\varepsilon_{r\infty}$: relative dielectric constant at high frequency limit
τ: relaxation time [s]
β: constant representing distribution of relaxation time
$\sigma_0$: DC conductivity [S/m]
$\varepsilon_0$: dielectric constant of vacuum
π: circumference ratio
f: frequency FIGS. 7A and 7B are diagrams each illustrating comparison of a curve obtained by fitting the above-described theoretical formula with values obtained by experiment. In FIG. 7A, the horizontal axis indicates the frequency [Hz], and the vertical axis indicates the relative dielectric constant $\varepsilon_r'$. In FIG. 7B, the horizontal axis indicates the frequency [Hz], and the vertical axis indicates the relative dielectric loss factor $\varepsilon_r''$. As illustrated in FIG. 7A, the theoretical value can express a tendency of the experimental value for the relative dielectric constant by fitting. As illustrated in FIG. 7B, the theoretical value can also express a tendency of the experimental value for the relative dielectric loss factor by fitting.

By fitting the above-described theoretical formula, as the parameters of the electrical characteristics related to the lubricant, the relative dielectric constant $\varepsilon_{r0}$ at the low frequency limit, the relative dielectric constant $\varepsilon_{r\infty}$ at the high frequency limit, the relaxation strength ($\varepsilon_{r0}-\varepsilon_{r\infty}$), the relaxation time $\tau$, the constant $\beta$ representing the distribution of the relaxation time, and the DC conductivity $\sigma_0$ can be derived. Note that the above-described theoretical formula is based on a Cole-Cole type theoretical formula and is merely an exemplary one. Therefore, the present invention is not limited to the theoretical formula, and other theoretical formulas may be used.

[Derivation of Parameters]

(Parameters Related to Electrical Characteristics)

Figure 8A:
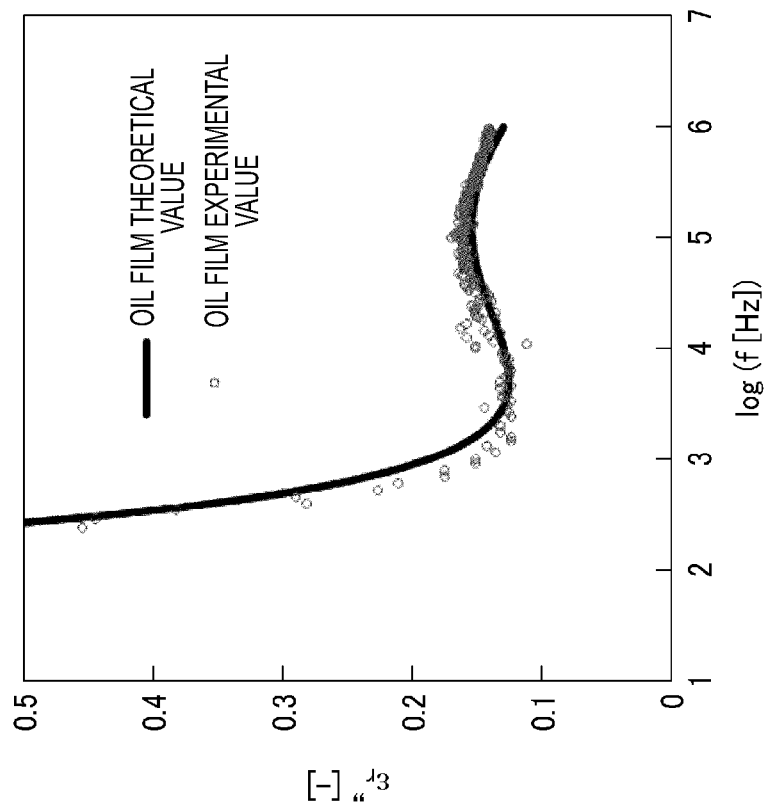
FIGS. 8A and 8B are diagrams each illustrating an example of parameter derivation by fitting to a theoretical formula.
Figure 8B:
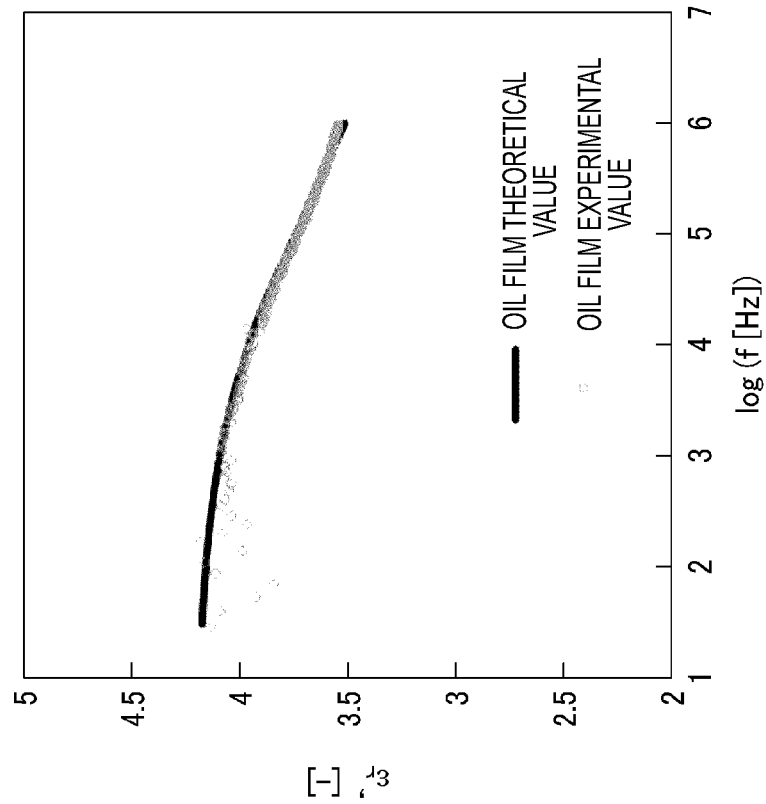

An example of deriving parameters related to electrical characteristics by the method described above will be described. FIGS. 8A and 8B each illustrate a curve of experimental results measured under the above-described test conditions and a curve of theoretical values obtained by fitting the experimental results to the theoretical formula. Herein, an example is illustrated where the oil film thickness h of the lubricant in the rolling bearing is assumed to be 250 nm. In FIG. 8A, the horizontal axis indicates the logarithm of the frequency [Hz], and the vertical axis indicates the relative dielectric constant $\varepsilon_r'$. In FIG. 8B, the horizontal axis indicates the logarithm of the frequency [Hz], and the vertical axis indicates the relative dielectric loss factor $\varepsilon_r''$.

FIG. 9 illustrates the relative dielectric constant, the relaxation strength, the relaxation time, the distribution of relaxation time, and the DC conductivity derived based on the fitted results illustrated in FIGS. 8A and 8B.

(Oil Film Thickness)

In the examples of FIGS. 8A, 8B, and 9, the oil film thickness h is set to 250 nm. In other words, when using the above-described formulas (11) and (12), it is necessary to set the oil film thickness h to calculate the relative dielectric constant $\varepsilon_r'$ and the relative dielectric loss factor $\varepsilon_r''$. In other words, the values of the relative dielectric constant $\varepsilon_r'$ and the relative dielectric loss factor $\varepsilon_r''$ change depending on the value of the oil film thickness h.

FIGS. 10A and 10B illustrate the experimental values obtained by setting different oil film thicknesses. Herein, three values of 200 nm, 250 nm, and 300 nm are used for comparison as the oil film thickness h. In FIG. 10A, the horizontal axis indicates the logarithm of the frequency [Hz], and the vertical axis indicates the relative dielectric constant $\varepsilon_r'$. In FIG. 10B, the horizontal axis indicates the logarithm of the frequency [Hz], and the vertical axis indicates the relative dielectric loss factor $\varepsilon_r''$.

As illustrated in FIGS. 10A and 10B, the values of the relative dielectric constant $\varepsilon_r'$ and the relative dielectric loss factor $\varepsilon_r''$ change as the oil film thickness h changes. On the other hand, even when the setting of the oil film thickness h is changed, there is no change in the tendency of change in experimental values obtained by sweeping the frequency. For example, as illustrated in FIG. 10A, with respect to the relative dielectric constant $\varepsilon_r'$, the amount of change due to the change in oil film thickness h is constant at any of the frequencies. Similarly, as illustrated in FIG. 10B, with respect to the relative dielectric loss factor $\varepsilon_r''$, the amount of change due to the change in oil film thickness h is constant at any of the frequencies.

It is considered that the parameters related to the electrical characteristics of the rolling bearing during rotation and the oil film thickness are simultaneously derived based on the above-described characteristics. Herein, the relative dielectric constant $\varepsilon_{r\infty}$ at the high frequency limit can be specified by the amount of thickening agent and the type of base oil constituting the lubricant. Therefore, first, the value of the relative dielectric constant $\varepsilon_{r\infty}$ at the high frequency limit is specified from the amount of the thickening agent in the lubricant used in the rolling bearing and the type of the base oil. Herein, the relative dielectric constant $\varepsilon_{r\infty}$ at the high frequency limit may be a value of the lubricant in a bulk state. Then, by setting the value of the relative dielectric constant $\varepsilon_{r\infty}$ at the high frequency limit as boundary conditions in formulas (13) and (14), the oil film thickness h can be uniquely specified, and curves corresponding to the experimental values can be specified. In other words, in the case of the example illustrated in FIG. 10A, the value of the relative dielectric constant $\varepsilon_r'$ at each frequency can be specified by specifying the right end position corresponding to the relative dielectric constant $\varepsilon_{r\infty}$ at the high frequency limit.

Figure 11A:
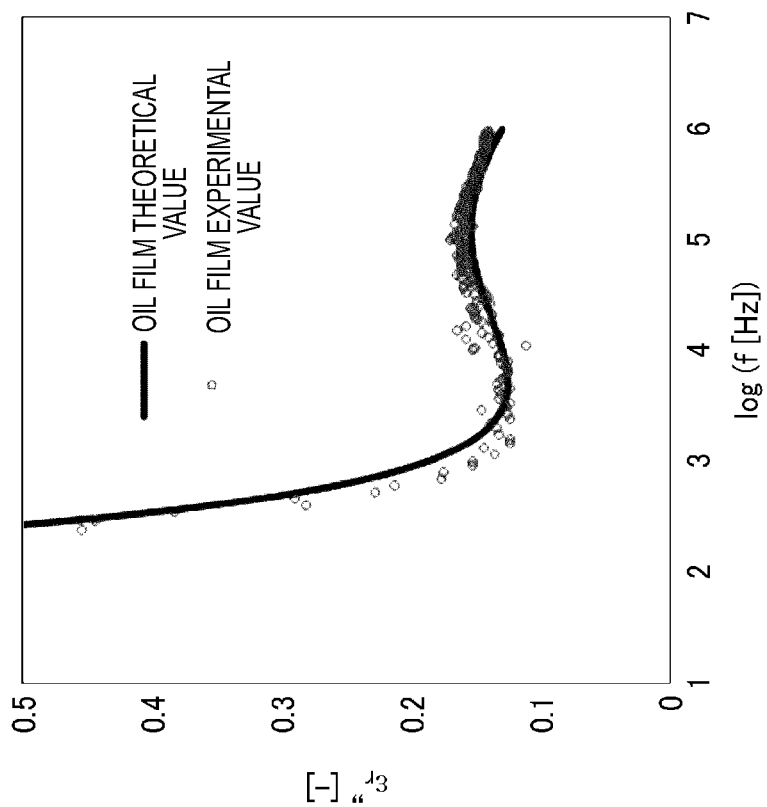
FIGS. 11A and 11B are diagrams each illustrating an example of oil film thickness and parameter derivation.
Figure 11B:
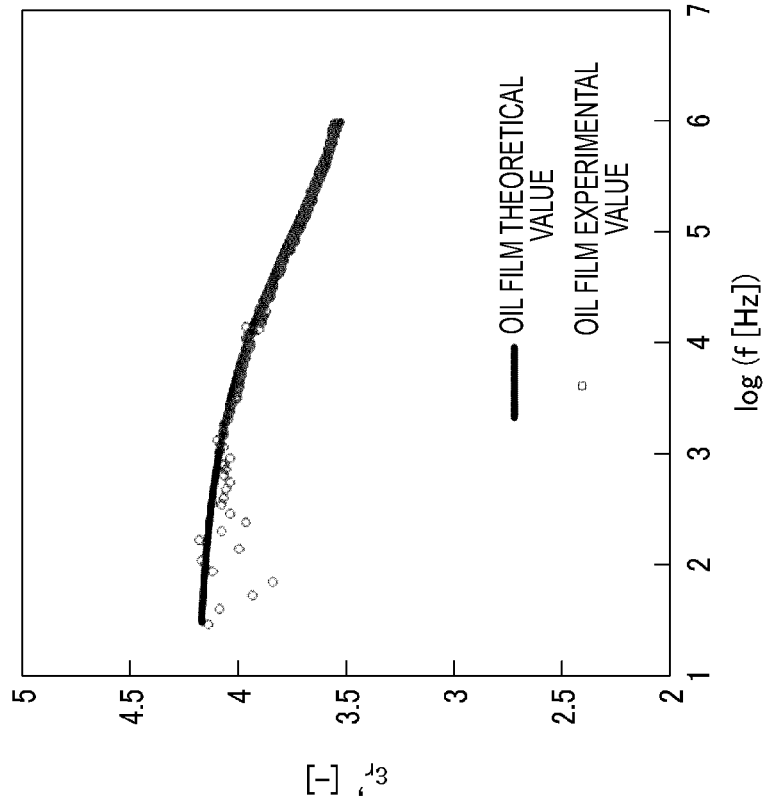

FIGS. 11A and 11B illustrate the experimental values obtained by specifying the value of the relative dielectric constant $\varepsilon_{r\infty}$ at the high frequency limit and the theoretical values by fitting. In FIG. 11A, the horizontal axis indicates the logarithm of the frequency [Hz], and the vertical axis indicates the relative dielectric constant $\varepsilon_r'$. In FIG. 11B, the horizontal axis indicates the logarithm of the frequency [Hz], and the vertical axis indicates the relative dielectric loss factor $\varepsilon_r''$. FIG. 12 illustrates the relative dielectric constant at the low frequency limit, the relaxation strength, the relaxation time, the distribution of relaxation time, and the DC conductivity derived based on the fitting results illustrated in FIGS. 11A and 11B. As described above, the value of the relative dielectric constant $\varepsilon_{r\infty}$ at the high frequency limit is determined based on the composition of the lubricant, and herein, the value in the bulk state is used.

As a result, the relative dielectric constant at the low frequency limit, the relaxation strength, the relaxation time, the distribution of relaxation time, the DC conductivity, and the oil film thickness can be derived simultaneously.

[Processing Flow]

Figure 13:
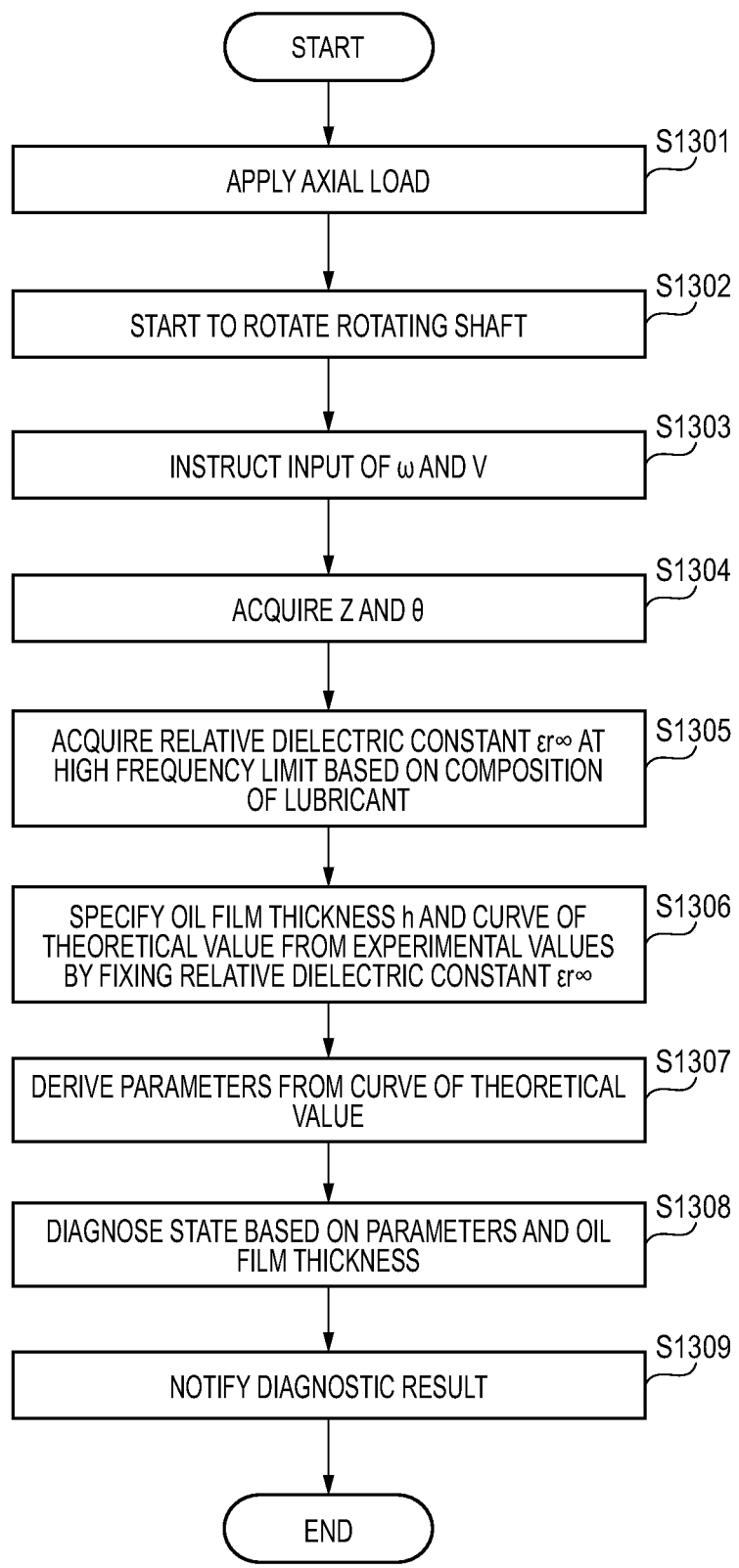
FIG. 13 is a flowchart of processing during measurement according to the present invention.

FIG. 13 is a flowchart of a state diagnosis process according to the present embodiment. The process is executed by the diagnosis device 1, and for example, a control device (not illustrated) included in the diagnosis device 1 may read a computer program for realizing the processing according to the present embodiment from a storage device (not illustrated) and execute the computer program to realize the process.

At S1301, the diagnosis device 1 controls the bearing device 2 so that the axial load is applied in a predetermined load direction. Note that the control of applying the axial load may be performed by a device other than the diagnosis device 1. Here, the phase and the impedance in a static contact state are measured.

At S1302, the diagnosis device 1 allows the motor 10 to start the rotation of the rotating shaft 7. Accordingly, the rotation of the inner ring 4 connected to the rotating shaft 7 is started. Note that the control of the motor 10 may be performed by a device other than the diagnosis device 1.

In S1303, the diagnosis device 1 controls the LCR meter 8 to apply the AC voltage V having the angular frequency $\omega$ to the bearing device 2 by using an AC power supply (not illustrated) provided in the LCR meter 8. Accordingly, the AC voltage V having the angular frequency $\omega$ is applied to the bearing device 2.

At S1304, the diagnosis device 1 acquires the impedance |Z| and the phase angle $\theta$ from the LCR meter 8 as outputs for the input in S1303. That is, the LCR meter 8 outputs the impedance |Z| and the phase angle $\theta$ to the diagnostic device 1, as a result of the detection of the bearing device 2 for the input AC voltage V and the angle frequency ω of the AC voltage.

At S1305, the diagnosis device 1 acquires the value of the relative dielectric constant $\varepsilon_{r\infty}$ at the high frequency limit based on the composition of the lubricant used in the bearing device 2. Note that the value of the relative dielectric constant $\varepsilon_{r\infty}$ at the high frequency limit is assumed to be defined in advance according to a composition of the lubricant. Information on the relative dielectric constant $\varepsilon_{r\infty}$ at the high frequency limit may be stored in a storage device (not illustrated) of the diagnosis device 1 or may be configured so that a user can individually set the information.

In S1306, the diagnostic apparatus 1 specifies a curve corresponding to the oil film thickness h and the theoretical value by using the impedance |Z| and the phase angle θ acquired in S1304, the information on the AC voltage V at the angular frequency ω indicated in S1303, and the value of the relative dielectric constant $\varepsilon_{r\infty}$ at the high frequency limit acquired in S1305. Specifically, the oil film thickness h and the curve illustrated in FIGS. 11A and 11B are obtained by fitting the experimental values by using the formulas (13) to (15) described above.

At S1307, the diagnostic apparatus 1 derives various parameters from the curve obtained as the result of the fitting in S1306. In the present embodiment, the relative dielectric constant at the low frequency limit, the relaxation strength, the relaxation time, the distribution of relaxation time, and the DC conductivity are obtained.

At S1308, the diagnosis device 1 diagnoses the state of the lubricant based on the oil film thickness specified in S1306 and various parameters derived in S1307. Although the content of diagnosis herein is not particularly limited, for example, a threshold may be set for each parameter, and whether the state is abnormal may be diagnosed by comparison with the thresholds. The plurality of thresholds may be set according to a degree of urgency of the abnormality, and the degree of urgency may be diagnosed by comparing with the thresholds.

In S1309, the diagnosis device 1 notifies the user of the diagnostic result obtained in S1308. Although a notification method herein is not particularly limited, for example, the parameters or items determined to be abnormal may be displayed on a screen or notified by voice. Then, the processing flow is ended.

As described above, according to the present embodiment, even when it is difficult to actually measure the thickness of the oil film of the lubricant in the rolling bearing or the like, the thickness of the oil film can be specified, and the parameters related to the electrical characteristics according to the oil film can be derived. Then, based on such values, the state diagnosis can be easily performed.

Note that, in the above-described example, various parameters are derived by setting the relative dielectric constant $\varepsilon_{r\infty}$ at the high frequency limit. However, the present invention is not limited thereto. For example, the above-described formulas (7) and (8) are functions including the oil film thickness h. Herein, since the oil film thickness h is a parameter that does not change depending on the angular frequency ω of the AC voltage, a formula having a configuration of deriving the dielectric constant with dh/dω=0 may be used. In some configurations, the oil film thickness h may be calculated based on operating conditions and design parameters of the rolling bearing, and various parameters may be calculated by using the value.

OTHER EMBODIMENTS

In the above-described embodiment, the bearing device is described as an exemplary one, but the present invention is not limited thereto. As illustrated in FIGS. 2 to 5, the present invention can be applied to other devices by setting a geometric model and equivalent circuit. For example, the oil film thickness of the lubricant in the rolling bearing described in the first embodiment is assumed to be on an order of μm to nm. Therefore, a method according to the present invention may be applied when measuring substances in such sizes. A method according to the present invention can be applied to a rolling device using a lubricant as an applicable device.

The present invention can also be realized by processes in which computer programs or applications for implementing the functions of one or more embodiments described above is supplied to a system or device by using a network, a storage medium, or the like, and one or more processors in a computer of the system or device reads and executes the computer programs.

The present invention may also be realized by a circuit (for example, an application specific integrated circuit (ASIC) or a field programmable gate array (FPGA)) implementing one or more functions.

As described above, the present invention is not limited to the above-described embodiments, and those skilled in the art can make modifications and applications by combining the respective configurations of the embodiments with each other or based on the description of the specification and well-known techniques, which are also contemplated by the present invention and falls within the scope of protection of the present invention.

As described above, the present specification discloses the following matters.

(1) A state detection method for detecting an oil film state according to a lubricant in a device configured to lubricate a plurality of parts with the lubricant, the method including:

a measurement step of measuring impedance and a phase angle of an electric circuit by applying an AC voltage to the electric circuit configured with the plurality of parts while changing a frequency; and a derivation step of deriving an oil film thickness according to the lubricant and a parameter indicating an electrical characteristic according to the oil film thickness, based on a relative dielectric constant at a high frequency limit of the lubricant defined based on a composition of the lubricant, and the impedance and the phase angle measured in the measurement step.

According to the present configuration, it is possible to provide a method for simultaneously deriving the film thickness of the lubricant in the device and the parameter related to the electrical characteristic according to the film thickness.

(2) The state detection method according to (1), in which the relative dielectric constant at the high frequency limit of the lubricant is a relative dielectric constant at the high frequency limit of the lubricant in a bulk state.

According to the present configuration, by using the relative dielectric constant of the lubricant in a bulk state at the high frequency limit, it is possible to easily and simultaneously derive the film thickness of the lubricant in the device and the parameter related to the electrical characteristic according to the film thickness.

(3) The state detection method according to (1) or (2), in which the parameter includes at least one of a relative dielectric constant at a low frequency limit, a relaxation strength, a relaxation time, a distribution of relaxation time, and DC conductivity.

According to the present configuration, it is possible to derive the relative dielectric constant at the low frequency limit, the relaxation strength, the relaxation time, the distribution of relaxation time, and the DC conductivity as the parameter according to the state of the lubricant in the device.

(4) The state detection method according to any one of (1) to (3), in which the device is a rolling device.

According to the present configuration, for the rolling device, it is possible to simultaneously derive the film thickness of the lubricant in the rolling device and the parameter related to the electrical characteristic according to the film thickness.

(5) The state detection method according to any one of (1) to (3), in which the device is a bearing device, and
the plurality of parts include an outer member, an inner member, and a rolling element.

According to the present configuration, for the rolling bearing, it is possible to simultaneously derive the film thickness of the lubricant in the rolling bearing and the parameter related to the electrical characteristic according to the film thickness.

(6) The state detection method according to any one of (1) to (5), further including a diagnosis step of diagnosing a state of the device by using the oil film thickness and the parameter derived in the derivation step.

According to the present configuration, it is possible to diagnose the state of the device based on the derived oil film thickness and the parameter of the lubricant.

(7) A state detection device configured to detect an oil film state according to a lubricant in a device configured to lubricate a plurality of parts with the lubricant, the device including:
a measurement unit configured to measure impedance and a phase angle of an electric circuit by applying an AC voltage to the electric circuit configured with the plurality of parts while changing a frequency; and
a derivation unit configured to derive an oil film thickness according to the lubricant and a parameter indicating an electrical characteristic according to the oil film thickness, based on a relative dielectric constant at a high frequency limit of the lubricant defined based on a composition of the lubricant, and the impedance and the phase angle measured in by the measurement unit.

According to the present configuration, it is possible to provide a device for simultaneously deriving the film thickness of the lubricant in the device and the parameter related to the electrical characteristic according to the film thickness.

(8) A non-transitory computer-readable storage medium storing a computer program for causing a computer to execute:
a measurement step of measuring impedance and a phase angle of an electric circuit by applying an AC voltage to the electric circuit configured with a plurality of parts while changing a frequency for a device configured to lubricate the plurality of parts with a lubricant; and
a derivation step of deriving an oil film thickness according to the lubricant and a parameter indicating an electrical characteristic according to the oil film thickness, based on a relative dielectric constant at a high frequency limit of the lubricant defined based on a composition of the lubricant, and the impedance and the phase angle measured in the measurement step.

According to the present configuration, it is possible to provide a medium storing a program for simultaneously deriving the film thickness of the lubricant in the device and the parameter related to the electrical characteristic according to the film thickness.

Heretofore, although various embodiments have been described with reference to the drawings, it goes without saying that the present invention is not limited to such examples. It is obvious that persons skilled in the art can conceive of various changes or modifications within the scope disclosed in the claims, and it is understood that the changes or modifications also belong to the technical scope of the present invention. Components in the above-described embodiments may be combined arbitrarily without departing from the spirit of the invention.

Note that the present application is based on Japanese patent application (Japanese Patent Application No. 2020-163963) filed on Sep. 29, 2020 and Japanese patent application (Japanese Patent Application No. 2021-137564) filed on Aug. 25, 2021, contents of which are incorporated by reference into the present application.

REFERENCE SIGNS LIST

1: diagnosis device
2: bearing device
3: outer ring (outer member)
4: inner ring (inner member)
5: rolling element
6: seal
7: rotating shaft
8: LCR meter
9: rotation connector
10: motor

The invention claimed is:

1. A state detection method for detecting an oil film state according to a lubricant in a device configured to lubricate a plurality of parts with the lubricant, the method comprising:
a measurement step of measuring impedance and a phase angle of an electric circuit by applying an AC voltage to the electric circuit configured with the plurality of parts while changing a frequency; and
a derivation step of deriving an oil film thickness according to the lubricant and a parameter indicating an electrical characteristic according to the oil film thickness, based on a relative dielectric constant at a high frequency limit of the lubricant defined based on a composition of the lubricant, and the impedance and the phase angle measured in the measurement step,
wherein the relative dielectric constant at the high frequency limit of the lubricant is a relative dielectric constant at the high frequency limit of the lubricant in a bulk state.

2. The state detection method according to claim 1, wherein the parameter includes at least one of a relative dielectric constant at a low frequency limit, a relaxation strength, a relaxation time, a distribution of relaxation time, and DC conductivity.

3. The state detection method according to claim 1, wherein the device is a rolling device.

4. The state detection method according to claim 1, wherein
the device is a bearing device, and
the plurality of parts include an outer member, an inner member, and a rolling element.

5. The state detection method according to claim 1, further comprising a diagnosis step of diagnosing a state of the device by using the oil film thickness and the parameter derived in the derivation step.

6. A state detection method for detecting an oil film state according to a lubricant in a device configured to lubricate a plurality of parts with the lubricant, the method comprising:
- a measurement step of measuring impedance and a phase angle of an electric circuit by applying an AC voltage to the electric circuit configured with the plurality of parts while changing a frequency; and
- a derivation step of deriving an oil film thickness according to the lubricant and a parameter indicating an electrical characteristic according to the oil film thickness, based on a relative dielectric constant at a high frequency limit of the lubricant defined based on a composition of the lubricant, and the impedance and the phase angle measured in the measurement step,
- wherein the parameter includes at least one of a relative dielectric constant at a low frequency limit, a relaxation strength, a relaxation time, a distribution of relaxation time, and DC conductivity.

* * * * *